United States Patent
Knobloch

(10) Patent No.: US 12,394,058 B2
(45) Date of Patent: Aug. 19, 2025

(54) GENERATION OF RADIOLOGICAL IMAGES

(71) Applicant: BAYER AKTIENGESELLSCHAFT, Leverkusen (DE)

(72) Inventor: Gesine Knobloch, Berlin (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 428 days.

(21) Appl. No.: 17/907,556

(22) PCT Filed: Mar. 25, 2021

(86) PCT No.: PCT/EP2021/057689
§ 371 (c)(1),
(2) Date: Sep. 28, 2022

(87) PCT Pub. No.: WO2021/197996
PCT Pub. Date: Oct. 7, 2021

(65) Prior Publication Data
US 2023/0147968 A1    May 11, 2023

(30) Foreign Application Priority Data

Apr. 3, 2020 (EP) .................................. 20167879
Oct. 29, 2020 (EP) .................................. 20204511

(51) Int. Cl.
G06T 7/00 (2017.01)
G01R 33/56 (2006.01)
(Continued)

(52) U.S. Cl.
CPC ........ G06T 7/0016 (2013.01); G01R 33/5601 (2013.01); G01R 33/5608 (2013.01);
(Continued)

(58) Field of Classification Search
CPC ............... G06T 7/0016; G06T 11/00; G06T 2207/10016; G06T 2207/10088;
(Continued)

(56) References Cited

U.S. PATENT DOCUMENTS

| 732,697 A | 7/1903 | Bates |
|---|---|---|
| 5,732,697 A | 3/1998 | Zhang et al. |

(Continued)

FOREIGN PATENT DOCUMENTS

| CN | 104769641 A | 7/2015 |
|---|---|---|
| CN | 107492090 A | 12/2017 |

(Continued)

OTHER PUBLICATIONS

Thompson; et al, "Indicator Transit Time Considered as a Gamma Variate", Circulation Research, Jun. 1964, vol. XIV, 502-515.
(Continued)

Primary Examiner — Shefali D Goradia
(74) Attorney, Agent, or Firm — Alexandria Quezada; David Schramm

(57) ABSTRACT

The disclosure relates to the generation of radiological images of an examination area of an object under examination. On the basis of measured radiological images of an examination area that show blood vessels in the examination area with decreasing contrast intensity over time, the disclosure generates artificial radiological images of the examination area that show blood vessels with constant contrast intensity.

12 Claims, 8 Drawing Sheets

Figure 1:
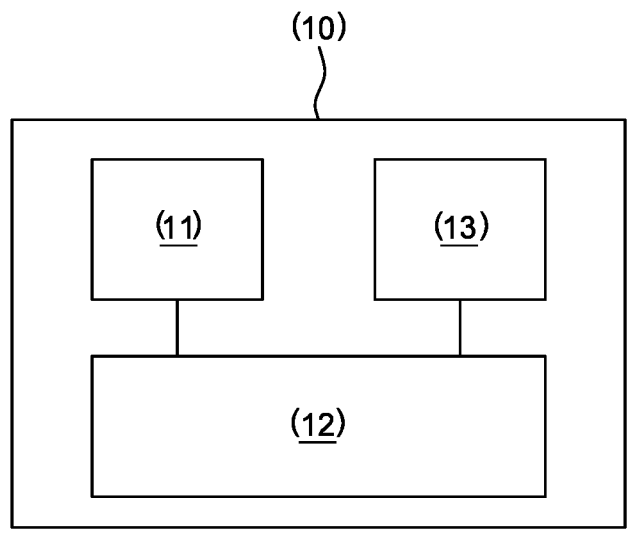

(51) Int. Cl.
*G06T 11/00* (2006.01)
*G16H 50/50* (2018.01)

(52) U.S. Cl.
CPC ............. *G06T 11/00* (2013.01); *G16H 50/50* (2018.01); *G06T 2207/10016* (2013.01); *G06T 2207/10088* (2013.01); *G06T 2207/20081* (2013.01); *G06T 2207/20084* (2013.01); *G06T 2207/30101* (2013.01); *G06T 2210/41* (2013.01)

(58) Field of Classification Search
CPC . G06T 2207/20081; G06T 2207/20084; G06T 2207/30101; G06T 2210/41; G16H 50/50; G01R 33/5601; G01R 33/5608
See application file for complete search history.

(56) References Cited

U.S. PATENT DOCUMENTS

| | | | |
|---|---|---|---|
| 5,840,026 A | 11/1998 | Uber, III et al. | |
| 6,039,931 A | 3/2000 | Schmitt-Willich et al. | |
| 6,643,537 B1 | 11/2003 | Zatezalo et al. | |
| 6,754,376 B1 | 6/2004 | Turek et al. | |
| 6,819,790 B2 | 11/2004 | Suzuki et al. | |
| 7,564,990 B2 | 7/2009 | Kern et al. | |
| 7,738,683 B2 | 6/2010 | Cahill et al. | |
| 7,853,309 B2 * | 12/2010 | Ichihara | A61B 6/481 600/407 |
| 7,937,134 B2 | 5/2011 | Uber et al. | |
| 7,949,167 B2 | 5/2011 | Krishnan et al. | |
| 8,060,178 B2 | 11/2011 | Zhou et al. | |
| 8,155,406 B2 | 4/2012 | Mattiuzzi | |
| 9,311,702 B2 | 4/2016 | Pautot | |
| 9,449,381 B2 | 9/2016 | Liang | |
| 9,616,166 B2 | 4/2017 | Kalafut et al. | |
| 9,754,371 B2 | 9/2017 | Kateb et al. | |
| 9,959,615 B2 | 5/2018 | Liang et al. | |
| 10,157,467 B2 | 12/2018 | Dincer et al. | |
| 10,176,408 B2 | 1/2019 | Paik et al. | |
| 10,335,106 B2 | 7/2019 | Kim | |
| 10,555,773 B2 | 2/2020 | Higaki et al. | |
| 10,634,753 B2 | 4/2020 | De Weerdt | |
| 10,645,359 B2 | 5/2020 | Bist et al. | |
| 10,933,186 B2 | 3/2021 | Uber, III | |
| 11,246,558 B2 | 2/2022 | Uber, III et al. | |
| 11,308,613 B2 | 4/2022 | Chitiboi et al. | |
| 2005/0100208 A1 | 5/2005 | Suzuki et al. | |
| 2006/0018524 A1 | 1/2006 | Suzuki et al. | |
| 2007/0047787 A1 | 3/2007 | Oakley et al. | |
| 2008/0247622 A1 | 10/2008 | Aylward et al. | |
| 2008/0317315 A1 | 12/2008 | Stemmer | |
| 2009/0143669 A1 | 6/2009 | Harms et al. | |
| 2010/0198054 A1 | 8/2010 | Ewing et al. | |
| 2011/0029248 A1 | 2/2011 | Saeed et al. | |
| 2013/0035921 A1 | 2/2013 | Rodriguez-Ponce et al. | |
| 2013/0297554 A1 | 11/2013 | Mah | |
| 2014/0062481 A1 | 3/2014 | Greiser et al. | |
| 2014/0257854 A1 | 9/2014 | Becker et al. | |
| 2015/0125398 A1 | 5/2015 | Assouline et al. | |
| 2016/0000945 A1 | 1/2016 | Nedergaard et al. | |
| 2016/0035093 A1 | 2/2016 | Kateb et al. | |
| 2016/0038092 A1 | 2/2016 | Golay | |
| 2016/0109539 A1 | 4/2016 | Mardor et al. | |
| 2017/0065241 A1 * | 3/2017 | Hoernig | A61B 6/5235 |
| 2017/0243349 A1 | 8/2017 | Hou et al. | |
| 2017/0245817 A1 | 8/2017 | Berlin et al. | |
| 2017/0269182 A1 | 9/2017 | Beck | |
| 2017/0281278 A1 | 10/2017 | Higaki et al. | |
| 2018/0242917 A1 | 8/2018 | Bagherzadeh et al. | |
| 2018/0303960 A1 | 10/2018 | Meijer et al. | |
| 2018/0315183 A1 | 11/2018 | Milioni De Carvalho et al. | |
| 2018/0374246 A1 * | 12/2018 | Igarashi | A61B 5/0042 |
| 2019/0012932 A1 | 1/2019 | Higaki et al. | |
| 2019/0099145 A1 | 4/2019 | Kim | |
| 2019/0122348 A1 * | 4/2019 | Jensen | G16H 50/50 |
| 2019/0310338 A1 | 10/2019 | James et al. | |
| 2019/0317171 A1 | 10/2019 | Nayak et al. | |
| 2019/0318474 A1 | 10/2019 | Han | |
| 2019/0362522 A1 * | 11/2019 | Han | A61B 5/055 |
| 2019/0365340 A1 | 12/2019 | Hao et al. | |
| 2020/0134876 A1 * | 4/2020 | Park | G06F 18/214 |
| 2020/0167911 A1 | 5/2020 | Park et al. | |
| 2020/0202557 A1 | 6/2020 | Schmidt | |
| 2020/0242744 A1 | 7/2020 | Schafer et al. | |
| 2020/0258629 A1 | 8/2020 | Ahmad et al. | |
| 2020/0311932 A1 * | 10/2020 | Hooper | G06F 18/2413 |
| 2020/0333414 A1 * | 10/2020 | Hilbert | G06T 5/50 |
| 2020/0371182 A1 | 11/2020 | Grimm et al. | |
| 2021/0012486 A1 | 1/2021 | Huang et al. | |
| 2021/0027436 A1 | 1/2021 | Banerjee et al. | |
| 2021/0027502 A1 | 1/2021 | Abumoussa et al. | |
| 2021/0056734 A1 | 2/2021 | Han | |
| 2021/0350935 A1 * | 11/2021 | Kinsey | G06N 3/088 |
| 2021/0386389 A1 | 12/2021 | Freiman et al. | |
| 2022/0018924 A1 | 1/2022 | Bai et al. | |
| 2022/0031270 A1 | 2/2022 | Cohen et al. | |
| 2022/0105265 A1 | 4/2022 | Cowan et al. | |
| 2022/0198734 A1 | 6/2022 | Kudo et al. | |
| 2022/0351369 A1 | 11/2022 | Haase et al. | |
| 2022/0409145 A1 * | 12/2022 | Knobloch | A61B 5/4244 |
| 2023/0243909 A1 * | 8/2023 | Hamilton | G01R 33/50 324/309 |

FOREIGN PATENT DOCUMENTS

| | | | | |
|---|---|---|---|---|
| CN | 108324244 A | 7/2018 | | |
| CN | 109983474 A | 7/2019 | | |
| EP | 1941460 A1 | 7/2008 | | |
| EP | 2626718 A1 | 8/2013 | | |
| EP | 2750102 A1 | 7/2014 | | |
| EP | 3118644 A1 | 1/2017 | | |
| EP | 3322997 A1 | 5/2018 | | |
| EP | 1941460 B1 | 12/2018 | | |
| EP | 3619631 A1 | 3/2020 | | |
| EP | 3804615 A1 | 4/2021 | | |
| EP | 3875979 A1 | 9/2021 | | |
| JP | 5281672 B2 * | 9/2013 | | A61B 6/504 |
| JP | 5878009 B2 | 3/2016 | | |
| KR | 102001398 B1 | 7/2019 | | |
| WO | 2007053676 A2 | 5/2007 | | |
| WO | 2009135923 A1 | 11/2009 | | |
| WO | 2012075577 A1 | 6/2012 | | |
| WO | 2013121374 A2 | 8/2013 | | |
| WO | 2014162273 A1 | 10/2014 | | |
| WO | 2016007734 A1 | 1/2016 | | |
| WO | 2017040152 A1 | 3/2017 | | |
| WO | 2017139110 A1 | 8/2017 | | |
| WO | 2018046412 A1 | 3/2018 | | |
| WO | 2018183044 A1 | 10/2018 | | |
| WO | 2018200493 A1 | 11/2018 | | |
| WO | 2018202541 A1 | 11/2018 | | |
| WO | 2019046299 A1 | 3/2019 | | |
| WO | 2019063520 A1 | 4/2019 | | |
| WO | WO-2019074938 A1 * | 4/2019 | | G06N 3/045 |
| WO | 2019102846 A1 | 5/2019 | | |
| WO | 2019204406 A1 | 10/2019 | | |
| WO | 2019241659 A1 | 12/2019 | | |
| WO | 2021052850 A1 | 3/2021 | | |
| WO | 2021069338 A1 | 4/2021 | | |
| WO | 2021069343 A1 | 4/2021 | | |
| WO | 2021197996 A1 | 10/2021 | | |
| WO | WO-2022184297 A1 * | 9/2022 | | A61B 6/032 |

OTHER PUBLICATIONS

Wang; et al, "Stacked Fully Convolutional Networks for Pulmonary Vessel Segmentation", IEEE Visual Communications and Image Processing (VCIP), 2018.

Weizman; et al, "Prediction of Brain MR Scans in Longitudinal Tumor Follow-Up Studies", Oct. 1, 2012, pp. 179-187.

"Written Opinion from PCT Application No. PCT/EP2021/057689", Jun. 24, 2021.

(56) References Cited

OTHER PUBLICATIONS

Xiao; Yu-Dong et al, "MRI contrast agents: Classification and application (Review)", International Journal of Molecular Medicine, 2016, 38, 1319-1326.

Yasaka Koichiro; et al, "Deep Learning with Convolutional Neural Network for Differentiation of Liver Masses at Dynamic Contrast-enhanced Ct: A Preliminary Study", Radiology, Mar. 2018, vol. 286; No. 3, 887-896.

Yasaka, et al., "Liver Fibrosis: Deep Convolutional Neural Network for Staging by Using Gadoxetic Acid-enhanced Hepatobiliary Phase MR Images", Dec. 14, 2017, Radiology, vol. 287, No. 1.

Karani Neerav et al: "Temporal Interpolation of Abdominal MRIs Acquired During Free-Breathing", Sep. 4, 2017 (Sep. 4, 2017), 12th European Conference on Computer Vision, ECCV 2012; [Lecture Notes in Computer Science], Springer Berlin Heidelberg, Berlin, Heidelberg, pp. 359-367, XP047528114, ISSN: 0302-9743 ISBN: 978-3-642-39453-9.

Qin Chen et al: "Convolutional Recurrent Neural Networks for Dynamic MR Image Reconstruction", IEEE Transactions on Medical Imaging, IEEE Service Center, Piscataway, NJ, US, Bd. 38, Nr. 1, Jan. 1, 2019 (Jan. 1, 2019), Seiten 280-290, P011694961, ISSN: 0278-0062, DOI: 10.1109/TMI.2018.2863670.

Takeshima, Hidenori: "Integrating Spatial and Temporal Correlations into a Deep Neural Network for Low-delay Reconstruction of Highly Undersampled Radial Dynamic Images", International Society for Magnetic Resonance in Medicine, ISMRM, 2030 Addison Street, 7th Floor, Berkeley, CA 94704 USA, pp. 2796, Jun. 1, 2018 (Jun. 1, 2018).

He, et al., "Deep Predictive Modeling of Dynamic Contrast-Enhanced MRI Data", Proc. Intl. Soc. Mag. Reson. Med., 2019, vol. 27.

Kurozumi, et al., "Evaluation of hemodynamic imaging findings of hypervascular hepatocellular carcinoma: comparison between dynamic contrast-enhanced magnetic resonance imaging using radial volumetric imaging breath-hold examination with k-space-weighted image contrast reconstruction and dynamic computed tomography during hepatic arteriography", Japanese Journal of Radiology, 2018, pp. 295-302, vol. 36.

Zhang, et al., "Dynamic contrast enhanced MR imaging for evaluation of angiogenesis of hepatocellular nodules in liver cirrhosis in N-nitrosodiethylamine induced rat model", Eur. Radiol., 2017, pp. 2086-2094, vol. 27.

Baccouche; et al, "Sequential Deep Learning for Human Action Recognition", International Workshop on Human Behavior Understanding, 2011, 29-39.

Bannas; et al, "Combined Gadoxetic Acid and Gadofosveset Enhanced Liver MRI: A Feasibility and Parameter Optimization Study", Magnetic Resonance in Medicine, 2016, 75, 318-328.

Baytas Inci M.; et al, "Patient Subtyping via Time-Aware LSTM Networks", 2017.

Bellani; Giacomo et al, "Epidemiology, Patterns of Care, and Mortality for Patients With Acute Respiratory Distress Syndrome in Intensive Care Unites in 50 Countries", JAMA, 2016.

Cannella; et al., "Common pitfalls when using the Liver Imaging Reporting and Data System (LI-RADS): lessons learned from a multi-year experience", Abdominal Imaging, Aug. 2, 2018, 43-53.

Caraiani; et al, "Description of Focal Liver Lesions With GD-EOB-DTPA Enhanced MRI", Clujul Medical, 2015, vol. 88 No. 4, 438-448.

Chibuzo; Abonyi et al, "Intravascular Contrast Media in Radiography: Historical Development & Review of Risk Factors for Adverse Reactions", South American Journal of Clinical Research, 2016, Vo. 3, Issue 1.

Chiusano; et al, "DCE-MRI Analysis Using Sparse Adaptive Representations", 2011, 67-74.

Choi; Jun-Ho et al, "EmbraceNet: A robust deep learning architecture for multimodal classification", Information Fusion, 2019, 51, 259-270.

Conversano; et al, "Hepatic Vessel Segmentation for 3D Planning of Liver Surgery: Experimental Evaluation of a New Fully Automatic Algorithm", Academic Radiology, Apr. 2011, vol. 18/ No. 4, 461-470.

Coulden; Richard, "State-of-the-Art Imaging Techniques in Chronic Thromboembolic Pulmonary Hypertension", Proceedings of the American Thoracic Society, 2006, vol. 3, 577-583.

Delcroix Marion; et al, "Chronic Thromboembolic Pulmonary Hypertension; Epidemiology and Risk Factors", Annals of the American Thoracic Society, Jul. 2016, vol. 13 Supp. 13, S201-S206.

"FDA Reclassification Letter regarding OsteoDetect", May 24, 2018.

Fischer; et al, "Ultra-high-field imaging of the biliary tract of 7 Tesla: initial results of Gd-EOB-DTPA-enhanced MRCP", Proc. Intl. Soc. Mag. Reson. Med., 2012, 20.

Frydrychowicz; et al, "Hepatobiliary MR Imaging with Gadolinium Based Contrast Agents", J Magn Reson Imaging, Mar. 2012, 35 (3), 492-511.

Galie Nazzareno; et al, "2015 ESC/ERS Guidelines for the diagnosis and treatment of pulmonary hypertension", European Heart Journal, Jan. 2016, vol. 37, Issue 1, 67-119.

Ghodasara; Satyam et al, "Quantifying Perfusion Properties with DCE-MRI Using a Dictionary Matching Approach", International Society for Magnetic Resonance in Medicine, ISMRM,, Jun. 1, 2018.

Gong Enhao; et al, "Deep Learning Enables Reduced Gadolinium Dose for Contrast-Enhanced Brain MRI", J. Magn. Reson. Imaging, 2018, 48, 330-340.

Hachulla; et al, "Dual-energy computed tomographic imaging of pulmonary hypertension", Swiss Medical Weekly, 2016, 146; w14328, 1-20.

Hope; et al, "Improvement of Gadoxetate Arterial Phase Capture With a High Spatio-Temporal Resolution Multiphase Three-Dimensional SPGR-Dixon Sequence", Journal of Magnetic Resonance Imaging, 2013, 38, 938-945.

Huang Gao.; et al, "Densely Connected Convolutional Networks", Jan. 28, 2018.

Ignee; Andre et al, "Ultrasound contrast agents", Endoscopic Ultrasound, Nov.-Dec. 2016, vol. 5, Issue 6, 355-362.

"Information on Primovist", 2016.

"International Preliminary Report on Patentability from PCT Application No. PCT/EP2020/075288", Mar. 31, 2022.

"International Preliminary Report on Patentability from PCT Application No. PCT/EP2020/075593", Mar. 31, 2022.

"International Preliminary Report on Patentability from PCT Application No. PCT/EP2020/077767", Apr. 12, 2022.

"International Preliminary Report on Patentability from PCT Application No. PCT/EP2020/077775", Apr. 12, 2022.

"International Preliminary Report on Patentability from PCT Application No. PCT/IB2020/058688", Mar. 31, 2022.

"International Preliminary Report on Patentability from PCT Application No. PCT/US2020/021861", Sep. 23, 2021.

"International Search Report and Written Opinion from PCT Application No. PCT/IB2020/058688", Dec. 9, 2020.

"Introduction to Multimodal Learning Model", DEV Community, Feb. 5, 2019.

Ji; et al, "3D Convolutional Neural Networks for Human Action Recognition", IEEE Transactions on Pattern Analysis and Machine Intelligence, Jan. 2013, vol. 35 No. 1, 221-231.

Karpathy; et al, "Large-scale Video Classification with Convolutional Neural Networks", Proceedings of the IEEE Conference on Computer Vision and Pattern Recognition, 2014, 1725-1732.

Khan; et al, "Chapter 3.3 "Neural Networks Basics"", A Guide to Convolutional Neural Networks for Computer Vision, Morgan & Claypool Publishers, 2018, pp. 36-39.

Kim; et al, "Arterial subtraction images of gadoxetate-enhanced MRI improve diagnosis of early-stage hepatocellular carcinoma", Journal of Hepatology, 2019, vol. 71, 534-542.

Kim; et al, "Gadoxetic acid-enhanced magnetic resonance imaging: Hepatocellular carcinoma and mimickers", Clinical and Molecular Hepatology, Sep. 2019, vol. 25 No. 3, 223-233.

(56) References Cited

OTHER PUBLICATIONS

Knobloch; et al, "Combined Gadoxetic Acid and Gadobenate Dimeglumine Enhanced Liver MRI for Liver Metastasis Detection: A Parameter Optimization Study", Proc. Intl. Soc. Mag. Reson. Med., 2018.

Kwon; et al, "Differentiation of small (less than or equal to cm) hepatocellular carcinomas from small benign nodules in cirrhotic liver on gadoxetic acid-enhanced and diffusion-weighted magnetic resonance images", Abdominal Imaging, Jul. 6, 2014, pp. 64-78.

Le; Quoc V., "A Tutorial on Deep Learning Part 2: Autoencoders, Convolutional Neural Networks and Recurrent Neural Networks", Oct. 20, 2015.

Lusic Hrvoje; et al, "X-Ray Computed Tomography Contrast Agents", Chem. Rev., 2013.

Marcan; et al, "Segmentation of hepatic vessels from MRI images for planning of electroporation-based treatments in the liver", Radiol. Oncol., 2014, 48 (3), 267-281.

Meng Qinxue; et al, "Relational Autoencoder for Feature Extraction", Feb. 9, 2018.

Moccia; et al, "Blood vessel segmentation algorithms - Review of methods, datasets and evaluation metrics", Computer Methods and Programs in Biomedicine, 2018, 158, 71-91.

Nouh Mohamed; et al, "Radiographic and magnetic resonances contrast agents: Essentials and tips for safe practices", World Journal of Radiology, Sep. 28, 2017, vol. 9, Issue 9, 339-349.

Rajpurkar; Pranav et al, "CheXNet: Radiologist-Level Pneumonia Detection on Chest X-Rays with Deep Learning", 2017.

Shtern; Alon, "Shape Correspondence Using Spectral Methods and Deep Learning Research Thesis", Aug. 2017.

Simonyan; et al, "Two-Stream Convolutional Networks for Action Recognition in Videos", Advances in Neural Information Processing Systems, 2013, 568-576.

Smith; Dana, "Artificial Intelligence Can Detect Alzheimer's Disease in Braine Scans Six Years Before a Diagnosis", Jan. 2, 2019.

Smits Loek; et al, "Evaluation of ultrasmall superparamagnetic iron-oxide (USPIO) enhanced MRI with ferumoxytol to quantify arterial wall inflammation", Atherosclerosis, 2017, 263, 211-218.

Tapson Victor; et al, "Incidence and Prevalence of Chronic Thromboembolic Pulmonary Hypertension", Proceedings of the American Thoracic Society, Sep. 7, 2006, vol. 3, 564-567.

\* cited by examiner

GENERATION OF RADIOLOGICAL IMAGES

CROSS REFERENCE TO RELATED APPLICATIONS

The present application is a U.S. national stage filing under 35 U.S.C. § 371 of International Application No. PCT/EP2021/057689, filed 25 Mar. 2021, which claims priority to European Patent Application No. EP 20167879.4 filed 3 Apr. 2020, and European Patent Application No. EP 20204511.8 filed 29 Oct. 2020, the disclosures of each of which are incorporated in their entirety herein by this reference.

The present disclosure relates to the generation of radiological images of an examination region of an examination object. On the basis of such measured radiological images of an examination region that show blood vessels in the examination region with contrast enhancement which decreases over time, the present disclosure generates artificial radiological images of the examination region that show blood vessels with unchanging contrast enhancement.

Radiology is a medical field which deals with imaging for diagnostic and therapeutic purposes.

Whereas X-radiation and films sensitive to X-radiation were formerly primarily used in medical imaging, radiology nowadays includes various different imaging methods such as computed tomography (CT), magnetic resonance imaging (MRI) or sonography.

With all these methods, use can be made of substances which facilitate the depiction or delimitation of certain structures in an examination object. Said substances are referred to as contrast agents.

In computed tomography, iodine-containing solutions are usually used as contrast agents. In magnetic resonance imaging (MRI), superparamagnetic substances (e.g. iron oxide nanoparticles, superparamagnetic iron-platinum particles (SIPPs)) or paramagnetic substances (e.g. gadolinium chelates, manganese chelates) are usually used as contrast agents.

Examples of contrast agents can be found in the literature (see, for example, A. S. L. Jascinth et al.: *Contrast Agents in computed tomography: A Review*, Journal of Applied Dental and Medical Sciences, 2016, Vol. 2, Issue 2, 143-149; H. Lusic et al.: *X-ray-Computed Tomography Contrast Agents*, Chem. Rev. 2013, 113, 3, 1641-1666; haps://www.radiology.wisc.edu/wp-content/uploads/2017/10/contrast-agents-tutorial.pdf, M. R. Nough et al.: *Radiographic and magnetic resonances contrast agents: Essentials and tips for safe practices*, World J Radiol. 2017 Sep. 28; 9(9): 339-349; L. C. Abonyi et al.: *Intravascular Contrast Media in Radiography: Historical Development & Review of Risk Factors for Adverse Reactions*, South American Journal of Clinical Research, 2016, Vol. 3, Issue 1, 1-10; ACR Manual on Contrast Media, 2020, ISBN: 978-1-55903-012-0; A. Ignee et al.: *Ultrasound contrast agents*, Endosc Ultrasound. 2016 November-December; 5(6): 355-362).

From their pattern of spreading in the tissue, contrast agents can be roughly divided into the following categories: extracellular contrast agents, intracellular contrast, and blood-pool contrast agents.

The extracellular MRI contrast agents include, for example, the gadolinium chelates gadobutrol (Gadovist®), gadoteridol (Prohance®), gadoteric acid (Dotarem®), gadopentetic acid (Magnevis®) and gadodiamide (Omnican®). The highly hydrophilic properties of said gadolinium chelates and their low molecular weight lead, after intravenous administration, to rapid diffusion into the interstitial space. After a certain, comparatively short period of circulation in the blood circulation system, they are excreted via the kidneys.

Intracellular contrast agents are taken up into the cells of tissues to a certain extent and subsequently excreted. Intracellular MRI contrast agents based on gadoxetic acid are, for example, distinguished by the fact that they are proportionately specifically taken up by liver cells, the hepatocytes, accumulate in the functional tissue (parenchyma) and enhance the contrasts in healthy liver tissue before they are subsequently excreted via the gallbladder into the faeces. Examples of such contrast agents based on gadoxetic acid are described in U.S. Pat. No. 6,039,931A; they are commercially available for example under the trade names Primovist® and Eovist®. A further MRI contrast agent having a lower uptake into the hepatocytes is gadobenate dimeglumine (Multihance®).

Blood-pool contrast agents, also referred to as intravascular contrast agents, are distinguished by a distinctly longer residence time in the blood circulation system in comparison with the extracellular contrast agents. Gadofosveset is, for example, an intravascular MRI contrast agent based on gadolinium. It has been used as the trisodium salt monohydrate form (Ablavar®). It binds to serum albumin, thereby achieving the long residence time of the contrast agent in the blood circulation system (half-life in the blood about 17 hours). However, Ablavar® was taken off the market in 2017. Another contrast agent authorized as blood-pool contrast agent for magnetic resonance imaging is not commercially available. Similarly, a contrast agent authorized as blood-pool contrast agent for computed tomography is not available on the market.

Thus, products authorized as blood-pool contrast agents for radiological examinations are not commercially available. When generating radiological images with a comparatively long acquisition time/scanning time, for example image acquisition under free breathing of thorax and abdomen to depict, for example, the vascular system (e.g. diagnostics for pulmonary embolism under free breathing in MRI), an extracellular contrast agent is eliminated comparatively rapidly from the blood vessel system, meaning that the contrast drops rapidly. It would be advantageous, however, to be able to maintain the contrast for a longer period of time.

The present disclosure attends to this problem. The present disclosure provides means which make it possible to simulate radiological images on the basis of a blood-pool contrast agent.

The present disclosure provides, in a first aspect, a computer-implemented method comprising the steps of
  receiving a sequence of measured radiological images, wherein the measured radiological images show an examination region of an examination object at different, consecutive time points after an administration of a contrast agent, wherein the contrast agent leads to a contrast enhancement of blood vessels in the examination region, wherein the contrast enhancement of the blood vessels in the measured radiological images decreases as time increases,
  calculating a sequence of artificial radiological images on the basis of the received radiological images, wherein the contrast enhancement of the blood vessels in the artificial radiological images remains unchanged over time,
  outputting the artificial radiological images.

The present disclosure further provides a computer system comprising
  a receiving unit
  a control and calculation unit and
  an output unit
  wherein the control and calculation unit is configured to prompt the receiving unit to receive a sequence of measured radiological images, wherein the measured radiological images show an examination region of an examination object at different, consecutive time points after an administration of a contrast agent, wherein the contrast agent leads to a contrast enhancement of blood vessels in the examination region, wherein the contrast enhancement of the blood vessels in the measured radiological images decreases as time increases,
  wherein the control and calculation unit is configured to calculate a sequence of artificial radiological images on the basis of the measured radiological images, wherein the contrast enhancement of the blood vessels in the artificial radiological images remains unchanged over time,
  wherein the control and calculation unit is configured to prompt the output unit to output the artificial radiological images.

The present disclosure further provides a computer program product comprising a computer program which can be loaded into a memory of a computer, where it prompts the computer to execute the following steps:
  receiving a sequence of measured radiological images, wherein the measured radiological images show an examination region of an examination object at different, consecutive time points after an administration of a contrast agent, wherein the contrast agent leads to a contrast enhancement of blood vessels in the examination region, wherein the contrast enhancement of the blood vessels in the measured radiological images decreases as time increases,
  calculating a sequence of artificial radiological images on the basis of the received radiological images, wherein the contrast enhancement of the blood vessels in the artificial radiological images remains unchanged over time,
  outputting the artificial radiological images.

The present disclosure further provides for the use of a contrast agent in a radiological examination method, wherein the radiological examination method comprises the following steps:
  administering the contrast agent into a blood vessel of a blood vessel system of an examination object,
  capturing a sequence of radiological images of an examination region of the examination object, wherein the radiological images show the examination region at different, consecutive time points after the administration of the contrast agent, wherein the contrast agent leads to a contrast enhancement of blood vessels in the examination region, wherein the contrast enhancement of the blood vessels in the radiological images falls as time increases,
  calculating a sequence of artificial radiological images on the basis of the captured radiological images, wherein the contrast enhancement of the blood vessels in the artificial radiological images remains unchanged over time, outputting the artificial radiological images.

The present disclosure further provides a contrast agent for use in a radiological examination method, wherein the radiological examination method comprises the following steps:
  administering the contrast agent into a blood vessel of a blood vessel system of an examination object,
  capturing a sequence of radiological images of an examination region of the examination object, wherein the radiological images show the examination region at different, consecutive time points after the administration of the contrast agent, wherein the contrast agent leads to a contrast enhancement of blood vessels in the examination region, wherein the contrast enhancement of the blood vessels in the radiological images falls as time increases,
  calculating a sequence of artificial radiological images on the basis of the captured radiological images, wherein the contrast enhancement of the blood vessels in the artificial radiological images remains unchanged over time,
  outputting the artificial radiological images.

The present disclosure further provides a kit comprising a contrast agent and the computer program product according to the disclosure.

Further subjects of the disclosure and preferred embodiments of the disclosure are found in the dependent claims, in the present description and in the drawings.

The disclosure will be more particularly elucidated below without distinguishing between the subjects of the disclosure (method, computer system, computer program product, use, contrast agent for use, kit). On the contrary, the following elucidations are intended to apply analogously to all the subjects of the disclosure, irrespective of in which context (method, computer system, computer program product, use, contrast agent for use, kit) they occur.

The present disclosure generates a sequence of artificial radiological images of an examination region of an examination object, wherein the artificial radiological images show the examination region after an administration of a blood-pool contrast agent, even though no blood-pool contrast agent was administered. In other words: the present disclosure simulates, on the basis of a sequence of measured radiological images of an examination region, a sequence of artificial radiological images of the examination region after administration of an intravascular contrast agent. In other words: the present disclosure generates, on the basis of a sequence of radiological images which show an examination region of an examination object, a sequence of artificial radiological images which show how the examination region would look if a blood-pool contrast agent had been administered. A radiologist is thus able to generate a sequence of radiological images of an examination region of an examination object that look as if the examination object had been administered a blood-pool contrast agent, without the radiologist having administered such an intravascular contrast agent.

Accordingly, the term "artificial radiological image after administration of an intravascular contrast agent" is synonymous with the term "artificial radiological image which shows how an examination region looks/would look after administration of an intravascular contrast agent".

The term "image" is used in this description for both measured and artificially generated (calculated) radiological depictions of an examination region.

The "examination object" is usually a living being, preferably a mammal, very particularly preferably a human.

Part of the examination object—the examination region—is subjected to a radiological examination. The "examination region", also called image volume or field of view (FOV), is in particular a volume which is imaged in radiological images. The examination region is typically defined by a radiologist, for example on an overview image (localizer). It is of course also possible for the examination region to alternatively or additionally be defined automatically, for example on the basis of a selected protocol. The examination region can be or comprise, for example, the liver or part of the liver, the lung or part of the lung, the heart or part of the heart, the aorta or part of the aorta, abdominal blood vessels, leg/pelvis blood vessels, the oesophagus or part of the oesophagus, the stomach or part of the stomach, the small intestine or part of the small intestine, the large intestine or part of the large intestine, the abdomen or part of the abdomen, the pancreas or part of the pancreas and/or some other part of the examination object.

The radiological examination is preferably an MRI examination. Accordingly, the at least one (measured) radiological image captured of the examination region is preferably an MRI image, and the at least one artificially generated radiological image is likewise an MRI image.

In a further preferred embodiment, the radiological examination is a CT examination; accordingly, the at least one (measured) radiological image captured of the examination region is a CT image in this embodiment, and the at least one artificially generated radiological image is likewise a CT image.

Measured radiological images/radiological images generated by measurement and artificially generated radiological images can be presented as two-dimensional images showing a sectional plane through the examination object. The radiological images can be presented as a stack of two-dimensional images, with each individual image of the stack showing a different sectional plane. The radiological images can be presented as three-dimensional images (3D images). In the interests of simpler illustration, the disclosure will be elucidated at some points in the present description on the basis of the presence of two-dimensional radiological images, without any wish, however, to restrict the disclosure to two-dimensional radiological images. It is clear to a person skilled in the art how it is possible to apply what is respectively described to stacks of two-dimensional images and to 3D images (see, in relation to this, for example M. Reisler, W. Semmler: *Magnetresonanztomographie* [Magnetic resonance imaging], Springer Verlag, 3rd edition, 2002, ISBN: 978-3-642-63076-7).

Usually, the measured radiological images are present as digital image files. The term "digital" means that the radiological images can be processed by a machine, generally a computer system. "Processing" is understood to mean the known methods for electronic data processing (EDP).

Digital image files can be present in various formats. For example, digital image files can be coded as raster graphics. Raster graphics consist of a grid arrangement of so-called picture elements (pixel) or volume elements (voxel), to which a color or a gray value is assigned in each case. The main features of a 2D raster graphic are therefore the image size (width and height measured in pixels, also informally called image resolution) and the colour depth. A color is usually assigned to a picture element of a digital image file. The color coding used for a picture element is defined, inter alia, in terms of the color space and the color depth. The simplest case is a binary image, in which a picture element stores a black-and-white value. In the case of an image, the color of which is defined in terms of the so-called RGB color space (RGB stands for the primary colors red, green and blue), each picture element consists of three subpixels, a subpixel for the color red, a subpixel for the color green and a subpixel for the color blue. The color of a picture element arises through the superimposition (additive blending) of the color values of the subpixels. The color value of a subpixel can, for example, be divided into 256 color nuances, which are called tonal values and usually range from 0 to 255. The color nuance "0" of each color channel is the darkest. If all three channels have the tonal value 0, the corresponding picture element appears black; if all three channels have the tonal value 255, the corresponding picture element appears white. When carrying out the present disclosure digital image files (radiological images) are subjected to certain operations. In this connection, the operations affect predominantly the picture elements, or the tonal values of the individual picture elements. There are a multiplicity of possible digital image formats and color codings. For simplification, it is assumed in this description that the present images are gray-scale raster graphics having a specific number of picture elements, with each picture element being assigned a tonal value indicating the gray value of the image. However, this assumption is not in any way to be understood as limiting. It is clear to a person skilled in the art of image processing how the teaching of said description can be applied to image files which are present in other image formats and/or in which the color values are coded differently.

In a first step, a sequence of measured radiological images is received. Said measured radiological images can be T1-weighted, T2-weighted and/or diffusion-weighted depictions and/or images that were generated with the aid of a different image-acquisition sequence.

A sequence of measured radiological images comprises at least two radiological images.

The term "sequence" means temporal sequence, i.e. multiple (at least two) radiological images showing the examination region at consecutive time points are generated by measurement. Each image is assigned a time point or each image can be assigned a time point. Usually, said time point is the time point at which the image was generated (absolute time). However, it is also conceivable for the radiological images to be assigned arbitrary time points (e.g. relative time points).

A person skilled in the art is aware that the generation of a radiological image takes a certain amount of time. An image can, for example, be assigned the time point of the start of image acquisition or the time point of the completion of image acquisition. A time point makes it possible to place a radiological image chronologically in relation to another radiological image; the time point of a radiological image makes it possible to establish whether the moment shown in the radiological image took place before or after a moment shown in another radiological image. Preferably, the radiological images are chronologically arranged in a sequence in such a way that images showing an earlier state of the examination region are arranged in the sequence before those images showing a later state of the examination region.

The time span between two immediately consecutive images in a sequence is preferably the same for all pairs of immediately consecutive images in the sequence, i.e. the images were preferably generated at a constant image-acquisition rate.

Preferably, the measured radiological images of the sequence show an examination region of an examination object at different, consecutive time points after an administration of a contrast agent, wherein the contrast agent leads to a contrast enhancement of blood vessels in the measured radiological images of the examination region, wherein the contrast enhancement of the blood vessels in the measured radiological images falls as time increases.

A sequence can also comprise a native radiological image (native image); such a native image shows the examination region in the absence of administration of a contrast agent.

The contrast agent administered can be an extracellular and/or an intracellular contrast agent. In a preferred embodiment, the contrast agent is an extracellular contrast agent. In a further preferred embodiment, the contrast agent is an intracellular contrast agent. In a first step, at least one first radiological image of the examination region can be captured without administration of a contrast agent (native image). The examination object is (in a further step) administered a contrast agent. The contrast agent can be an MRI contrast agent or a CT contrast agent. Preferably, the contrast agent is an extracellular MRI contrast agent such as gadobutrol, gadoteridol, gadoteric acid, gadopentetic acid and/or gadodiamide. Further extracellular MRI contrast agents have been described in the literature (see, for example, Yu.Dong Xiao et al.: MRI contrast agents: Classification and application (Review), International Journal of Molecular Medicine 38: 1326 (2016)).

In an alternative embodiment, the contrast agent is an intracellular MRI contrast agent such as, for example, Gd-EOB-DTPA (Primovist®), Mn-DPDP (mangafodipir), Gd-BOPTA (gadobenate dimeglumine) and/or Gd-DTPA mesoporphyrin (gadophrin). Further intracellular MRI contrast agents have been described in the literature (see, for example, Yu.Dong Xiao et al.: MRI contrast agents: Classification and application (Review), International Journal of Molecular Medicine 38: 1326 (2016)).

The contrast agent is preferably introduced into a blood vessel of the examination object, for example into an arm vein. From there, it moves with the blood along the blood circulation system.

The "blood circulation system" is the path covered by the blood in the body of humans and most animals. It is the flow system of the blood that is formed by the heart and by a network of blood vessels (cardiovascular system, blood vessel system).

Blood vessels can be divided into multiple types on the basis of their structure and their function: The arteries transport the blood under high pressure and at high flow velocity. Because of them, the blood passes from the heart into the various tissues. Branching off from the arteries are the arterioles, and they serve as control valves and have strong muscular walls which can constrict the vessels (vasoconstriction) or dilate them (vasodilatation). They branch further to form the capillaries, which perform the exchange of liquids, nutrients, electrolytes, hormones and other substances between blood and tissue and have a thin vascular wall permeable to substances of low molecular weight. In some organs (liver, spleen), the capillaries are widened and the endothelium becomes discontinuous; reference is then made to sinusoids. Venules have only a thin vascular wall; they collect the blood from the capillaries in order to supply it to the veins, which transport the blood from the periphery back to the heart. An extracellular contrast agent circulates in the blood circulation system for a period of time that is dependent on the examination object, the contrast agent and the administered amount, while it is continuously eliminated from the blood circulation system via the kidneys.

While the contrast agent spreads and/or circulates in the blood vessel system of the examination object, at least one radiological image of the blood vessel system or a portion thereof is captured. Preferably, at least one radiological image is captured of the portion of the blood vessel system that is situated in the examination region. Multiple radiological images can be captured that show different phases of the spreading of the contrast agent in the blood vessel system or a portion thereof (e.g. distribution phase, arterial phase, venous phase and/or the like). The capture of multiple images allows later differentiation of blood vessel types.

The measured radiological images show the blood vessel system or a portion thereof, in particular the portion situated in the examination region, with contrast enhancement compared to the surrounding tissue. Preferably, at least one first radiological image shows arteries with contrast enhancement (arterial phase), whereas at least one second radiological image shows veins with contrast enhancement (venous phase).

The measured radiological images are used as the basis for generation of artificial radiological images. The artificial radiological images preferably show the same examination region as the measured radiological images. If a plurality of measured radiological images of the examination region was captured at different time points after the administration of the contrast agent, the later radiological images in particular show blood vessels with an increasingly falling contrast compared to the surrounding tissue, since the contrast agent is gradually being eliminated from the blood vessels. By contrast, the artificial radiological images show the blood vessels with an unchangingly high contrast compared to the surrounding tissue.

The measured radiological images are used as the basis for generation of artificial radiological images with the aid of a computer system. It is conceivable that exactly one artificial radiological image is generated from each measured radiological image, the artificial radiological image showing the same examination region as the measured radiological image, and the artificial radiological image showing the examination region at the same time point as the measured radiological image, the difference being that the contrast enhancement in the measured radiological images decreases over time, whereas it remains unchanged (does not decrease) in the artificially generated radiological images.

This can be achieved in different ways.

In a preferred embodiment, a prediction model is used. The prediction model can have been trained on the basis of reference data to compensate for a contrast enhancement of blood vessels that falls over time. The prediction model can have been trained on the basis of reference data to generate, on the basis of a sequence of measured radiological images which show an examination region of an examination object after administration of an extracellular or an intracellular contrast agent, a sequence of artificial radiological images which show the examination region after administration of a blood-pool contrast agent. The prediction model can have been trained on the basis of reference data to generate, for a sequence of measured radiological images which show blood vessels in an examination region at different time points after an administration of a contrast agent, a sequence of artificial radiological images which show blood vessels in the examination region with contrast enhancement and with an unchanging contrast over time compared to the surrounding tissue.

The reference data which are used for training and validation of such a prediction model usually comprise measured radiological images of the examination region after the administration of an extracellular or intracellular contrast agent. The reference data can further comprise radiological images of the examination region after the administration of a blood-pool contrast agent. Such reference data can, for example, be ascertained in a clinical study. An intravascular contrast agent which can be used in such a clinical study is, for example, ferumoxytol. Ferumoxytol is a colloidal iron-carbohydrate complex which has been authorized for parenteral treatment of an iron deficiency in a chronic kidney disease when it is not possible to carry out an oral therapy. Ferumoxytol is administered as an intravenous injection. Ferumoxytol is commercially available as a solution for intravenous injection under the trade names Rienso® or Ferahme®. The iron-carbohydrate complex shows superparamagnetic properties and can therefore be used (off-label) for contrast enhancement in MRI examinations (see for example: L. P. Smits et al.: *Evaluation of ultrasmall superparamagnetic iron-oxide (USPIO) enhanced MRI with ferumoxytol to quantify arterial wall inflammation*, Atherosclerosis 2017, 263: 211-218). The present disclosure therefore further provides for the use of ferumoxytol, or another comparable blood-pool contrast agent which has been authorized for intravenous injection, as a blood-pool contrast agent for generation of a training data set for prediction of artificial radiological images after administration of a blood-pool contrast agent on the basis of measured radiological images after administration of an extracellular or an intracellular contrast agent. It is also conceivable to use already existing radiological images after administration of an intravascular contrast agent as training data, for example from the time when Ablavar® was still commercially available.

However, the reference data can also comprise artificially generated radiological images in which the contrast enhancement of the blood vessels that decreases over time in measured radiological images has been compensated for afterwards by image processing methods. Such image processing methods are known to a person skilled in the art (see, for example: M. A. Joshi: *Digital Image Processing—An Algorithmic Approach*, PHI Learning Private Limited, $2^{nd}$ Edition 2018, ISBN: 978-93-81472-58-7).

The prediction model can be trained in a supervised learning process to learn a relationship between the measured radiological images and the radiological images after administration of the blood-pool contrast agent or the images processed by means of image processing methods. This learned relationship can then be used in order to calculate artificial radiological images for newly measured radiological images, said artificial radiological images showing how the examination region would look after administration of a blood-pool contrast agent, although an extracellular contrast agent or an intracellular contrast agent was administered for the measured radiological images: blood vessels in the examination region show an unchanging enhanced contrast over time compared to the surrounding tissue. The prediction model is thus trained to compensate for the contrast enhancement of blood vessels that falls over time in measured radiological images.

The prediction model can, for example, be an artificial neural network or comprise such a network.

Such an artificial neural network comprises at least three layers of processing elements: a first layer with input neurons (nodes), an N-th layer with at least one output neuron (nodes) and N−2 inner layers, where N is a natural number and greater than 2.

The input neurons serve to receive measured (digital) radiological images as input values. Normally, there is one input neuron for each pixel or voxel of a digital radiological image. There can be additional input neurons for additional input values (e.g. information about the examination region, about the examination object and/or about conditions which prevailed when generating the radiological images).

In such a network, the output neurons serve to output (provide) the artificial radiological images.

The processing elements of the layers between the input neurons and the output neurons are connected to one another in a predetermined pattern with predetermined connection weights.

Preferably, the artificial neural network is a so-called convolutional neural network (CNN for short).

A convolutional neural network is capable of processing input data in the form of a matrix. This makes it possible to use digital radiological images represented as a matrix (e.g. width×height×color channels) as input data. By contrast, a normal neural network, for example in the form of a multilayer perceptron (MLP), requires a vector as input, i.e. to use a radiological image as input, the pixels or voxels of the radiological image would have to be rolled out successively in a long chain. As a result, normal neural networks are, for example, not capable of recognizing objects in a radiological image independently of the position of the object in the image. The same object at a different position in the image would have a completely different input vector.

A CNN consists essentially of filters (convolutional layer) and aggregation layers (pooling layer) which are repeated alternately and, at the end, of one layer or multiple layers of "normal" completely connected neurons (dense/fully connected layer).

When analyzing sequences (temporal sequences of multiple radiological images), space and time can be treated as equivalent dimensions and, for example, processed via 3D convolutions. This has, for example, been shown in the papers by Baccouche et al. (see, for example: *Sequential Deep Learning for Human Action Recognition; International Workshop on Human Behavior Understanding*, Springer 2011, pages 29-39) and Ji et al. (*3D Convolutional Neural Networks for Human Action Recognition*, IEEE Transactions on Pattern Analysis and Machine Intelligence, 35(1), 221-231). Furthermore, it is possible to train different networks responsible for time and space and to lastly merge the features, as described, for example, in publications by Karpathy et al. (see, for example *Large-scale Video Classification with Convolutional Neural Networks*; Proceedings of the IEEE conference on Computer Vision and Pattern Recognition, 2014, pages 1725-1732) and Simonyan & Zisserman (*Two-stream Convolutional Networks for Action Recognition in Videos*; Advances in Neural Information Processing Systems, 2014, pages 568-576).

Recurrent neural networks (RNNs) are a family of artificial neural networks which contain feedback connections between layers. RNNs allow the modelling of sequential data by common utilization of parameter data via different parts of the neural network. The architecture for an RNN contains cycles. The cycles represent the influence of a current value of a variable on its own value at a future time point, since at least a portion of the output data from the RNN is used as feedback for processing subsequent inputs in a sequence.

Details can be gathered from the prior art (see, for example: S. Khan et al.: *A Guide to Convolutional Neural Networks for Computer Vision*, Morgan & Claypool Publishers 2018, ISBN 1681730227, 9781681730226).

The training of the neural network can, for example, be carried out by means of a backpropagation method. The aim here in respect of the network is maximum reliability of mapping of given input vectors onto given output vectors. The mapping quality is described by an error function. The goal is to minimize the error function. In the case of the backpropagation method, an artificial neural network is taught by the alteration of the connection weights.

In the trained state, the connection weights between the processing elements contain information regarding the relationship between measured radiological images and artificially generated radiological images simulating radiological images after the administration of a blood-pool contrast agent. This information can be used in order to predict at least one artificial radiological image for at least one new measured radiological image.

A cross-validation method can be used in order to divide the data into training and validation data sets. The training data set is used in the backpropagation training of network weights. The validation data set is used in order to check the accuracy of prediction with which the trained network can be applied to unknown (new) radiological images.

However, a blood-pool contrast agent need not necessarily be/have been administered in order to generate a training and validation data set. It is also conceivable that a different contrast agent, preferably an extracellular contrast agent, is used to generate a training and validation data set. The contrast agent, even if it is not a blood-pool contrast agent, remains in the blood vessel system of the examination object for a certain time. This time may be sufficient for (measurement-based) capture of radiological images which show an examination region in which blood vessels have a high contrast compared to the surrounding tissue. These captured images can then, after any processing to compensate for the decrease in contrast enhancement over time, be used to train and validate a prediction model.

As already indicated, further information about the examination object, about the examination region and/or about examination conditions can also be used for training and validation of a prediction model and for generation of predictions using the prediction model.

Examples of information about the examination object are: sex, age, weight, height, anamnesis, nature and duration and amount of medicaments already ingested, blood pressure, central venous pressure, breathing rate, serum albumin, total bilirubin, blood sugar, iron content, breathing capacity and the like. These can, for example, also be gathered from a database or an electronic patient file.

Examples of information about the examination region are: pre-existing conditions, operations, partial resection, liver transplantation, iron liver, fatty liver and the like.

Preferably, the prediction model is taught to distinguish different blood vessels from one another, for example to distinguish arteries from veins. This can, for example, be done by a radiologist marking the respective blood vessels differently in the radiological images used for training. It is also conceivable that the prediction model learns to distinguish the different blood vessels from one another on the basis of the dynamics in a sequence of radiological images after the administration of a contrast agent. After administration in the form of a bolus, the contrast agent is not immediately present with the same concentration in all blood vessels, but spreads in the blood vessel system from the site of administration with the flow of blood. Depending on the site of administration, what are thus first passed through are the arteries or the veins. The prediction model can thus learn to distinguish different blood vessels from one another on the basis of the dynamic behavior of the administered contrast agent.

It is also conceivable that multiple radiological images are captured at different time points after the administration of the contrast agent, and said multiple radiological images are combined to form one image in which the blood vessels show a uniform and high contrast compared to the surrounding tissue.

An artificial radiological image can thus also be generated by adding up multiple measured radiological images which show the examination region at different time points after the administration of the contrast agent. It is, for example, conceivable that a first measured radiological image shows an arterial phase, whereas a second measured radiological image shows a venous phase. These two measured radiological images (and possibly further radiological images) can be added up. The adding up can be done pixel by pixel or voxel by voxel. For example, the gray values of the pixels can be added up (in pairs). Subsequent normalization can ensure that the gray values are back in the usual range (e.g. from 0 to 255).

If the examination object did not move during the acquisition of temporally consecutive radiological images, a pixel or voxel of one image exactly corresponds to a pixel or voxel of a following image and/or a preceding image: the corresponding pixels or voxels show the same examination region at different time points. In such a case, artificial radiological images can be calculated by carrying out the mathematical operations described in this description with the pairwise corresponding pixels or voxels. If the examination object did move between temporally consecutive radiological images, a movement correction must be performed before the described calculations are carried out. Movement correction methods are described in the prior art (see, for example: EP3118644, EP3322997, US20080317315, US20170269182, US20140062481, EP2626718).

The artificial radiological images generated according to the disclosure can be displayed on a monitor, output on a printer and/or stored in a data storage medium.

Preferably, artificial radiological images are automatically generated and output (preferably displayed) in quasi-real-time in addition to the corresponding measured radiological images or instead of the measured radiological images.

It is also conceivable that a blood vessel model is generated on the basis of the measured radiological images. The blood vessel model is a digital representation of the examination object or of part thereof (preferably the examination region), with structures which can be attributed to blood vessels having been marked in the representation, or structures which can be attributed to blood vessels being solely present in the representation. Preferably, the blood vessel model is a three-dimensional representation in which the spatial course of blood vessels has been marked/recorded. Preferably, different types of blood vessels (e.g. arteries and veins) have been marked differently.

In a preferred embodiment, the blood vessel model is generated on the basis of at least one measured native image and at least one measured radiological image after the administration of a contrast agent. The at least one native image shows an examination region of the examination object without contrast agent. The at least one radiological image after administration of a contrast agent preferably shows the same region, with some or all of the blood vessels in the region exhibiting contrast enhancement. By comparing the two images, it is possible to identify the structures in the radiological images that can be attributed to blood vessels.

The blood vessel model can be generated by subtraction of a native image from a measured radiological image after administration of a contrast agent and by subsequent normalization. The subtraction is preferably done pixel by pixel or voxel by voxel. For example, the gray values of the pixels can be subtracted from one another. The subsequent normalization ensures that the gray values are back in the usual range (e.g. from 0 to 255) and that there are no negative gray values.

If there are multiple radiological images after administration of a contrast agent that show the spreading of the contrast agent in the blood vessels at different time points, it is possible to identify different blood vessel types (e.g. arteries and veins). This allows differentiation and different marking of blood vessel types in the blood vessel model. In such a case, the blood vessel model can also be generated by adding up a plurality of measured radiological images after administration of a spreading contrast agent and by subsequent normalization. The adding up is preferably done pixel by pixel or voxel by voxel. For example, the gray values of the pixels can be added up in pairs. The subsequent normalization ensures that the gray values are back in the usual range (e.g. from 0 to 255).

Preferably, structures in the blood vessel model that cannot be attributed to blood vessels are removed: for example, if blood vessels are displayed brightly, then all pixels (or voxels) with gray values below a threshold value can be set to the gray value zero; by contrast, if blood vessels are displayed darkly, then all pixels (or voxels) with gray values above a threshold value can be set to the highest gray value (e.g. 255). By means of this procedure, structures not originating from blood vessels are reduced (in contrast) or completely eliminated.

The blood vessel model can also be obtained from measured radiological images by other segmentation methods. Segmentation methods are widely described in the literature. The following publications may be given as examples: F. Conversano et al.: *Hepatic Vessel Segmentation for 3D Planning of Liver Surgery*, Acad Radiol 2011, 18: 461-470; S. Moccia et al.: *Blood vessel segmentation algorithms—Review of methods, datasets and evaluation metrics*, Computer Methods and Programs in Biomedicine 158 (2018) 71-91; M. Marcan et al.: *Segmentation of hepatic vessels from MRI images for planning of electroporation-based treatments in the liver*, Radiol Oncol 2014; 48(3): 267-281; T. A. Hope et al.: *Improvement of Gadoxetate Arterial Phase Capture With a High Spatio-Temporal Resolution Multiphase Three-Dimensional SPGR-Dixon Sequence*, Journal of Magnetic Resonance Imaging 38: 938-945 (2013); WO2009/135923A1, U.S. Pat. No. 6,754,376B1, WO2014/162273A1, WO2017/139110A1, WO2007/053676A2, EP2750102A1).

Preferably, the blood vessel model is present in the same digital (data) format as the at least one measured radiological image after administration of a contrast agent and/or as the at least one native radiological image. If the same digital format is present, calculations can be performed more easily using the relevant files; in particular, the blood vessel model can be generated more easily from the measured radiological images.

The blood vessel model can be directly used and output as an artificial radiological image. However, it is also conceivable that one or more measured radiological images are superimposed on the blood vessel model in order to generate one or more artificial radiological images. For example, a native image can be superimposed in order to show the blood vessels in the native image. Preferably, different blood vessels can be faded in and out independently of one another. Analogously, at least one measured radiological image after administration of a contrast agent can also be superimposed on the blood vessel model. Superimposition of a radiological image after administration of a contrast agent is, for example, advantageous if small focal liver lesions are to be identified in an MRI examination of the liver (see, for example, P. Bannas: *Combined Gadoxetic Acid and Gadofosveset Enhanced Liver MRI: A Feasibility and Parameter Optimization Study*, Magnetic Resonance in Medicine 75:318-328 (2016)). It can be difficult to distinguish liver lesions from blood vessel structures in an MRI image. This can be remedied by the simulation of a blood-pool contrast agent that is according to the disclosure.

When superimposing the blood vessel model on at least one measured radiological image, preference is given to choosing different color values (false color display) for different types of blood vessels (e.g. arteries and veins). For example, it is possible in the artificial radiological image to mark arteries by means of a first color value (e.g. a color value for a red color) and veins by means of a second color value (e.g. a color value for a blue color).

Preferably, the pixels or voxels depicting blood vessels in the blood vessel model can be continuously faded into the at least one measured radiological image, for example by means of a (virtual) slider, with the corresponding pixels or voxels in the artificial radiological image thus generated increasingly assuming the color values of the pixels or voxels of the blood vessel model during fade-in. It is also conceivable that blood vessel types can be faded independently of one another (e.g. arteries independently of veins and/or veins independently of arteries). The option of switching on and off the structures originating from blood vessels or blood vessel types, instead of fading them in or in addition to fading them in, is conceivable, too.

In this way, a radiologist can visualize blood vessels or blood vessel types in a measured radiological image in order to be able to assign structures in the radiological images.

Further subjects of the disclosure and embodiments are:
1. A computer-implemented method comprising the steps of
    receiving at least one radiological image, wherein the at least one radiological image shows an examination region of an examination object,
    calculating at least one artificial radiological image on the basis of the at least one radiological image, wherein blood vessels in the at least one artificial radiological image are depicted with contrast enhancement compared to surrounding tissue,
    outputting the at least one artificial radiological image.
2. The method according to embodiment 1 above, comprising the steps of:
    receiving at least one measured radiological image, wherein the at least one measured radiological image shows an examination region of an examination object,
    supplying the at least one measured radiological image to a prediction model, wherein the prediction model has been trained on the basis of reference data in a supervised learning process to generate at least one artificial radiological image for at least one measured radiological image which shows an examination region of an examination object, wherein the at least one artificial radiological image shows the examination region after administration of a blood-pool contrast agent,
    receiving at least one artificial radiological image from the prediction model, wherein the at least one artificial radiological image shows the examination region after administration of a blood-pool contrast agent,
    outputting the at least one artificial radiological image.

3. The method according to either of embodiments 1 and 2 above, comprising the steps of
    receiving at least one measured radiological image, wherein the at least one measured radiological image is a radiological image or comprises an image which shows an examination region of an examination object after administration of a contrast agent,
    supplying the at least one measured radiological image to a prediction model, wherein the prediction model has been trained on the basis of reference data in a supervised learning process to generate at least one artificial radiological image for at least one measured radiological image which shows an examination region of an examination object after administration of a contrast agent, wherein the at least one artificial radiological image shows the examination region after administration of a blood-pool contrast agent,
    receiving at least one artificial radiological image from the prediction model, wherein the at least one artificial radiological image shows the examination region after administration of a blood-pool contrast agent,
    outputting the at least one artificial radiological image.
4. The method according to any of embodiments 1 to 3 above, comprising the steps of
    receiving a plurality of measured radiological images, wherein the radiological images show an examination region at different time points after an administration of a contrast agent,
    supplying the plurality of measured radiological images to a prediction model, wherein the prediction model has been trained on the basis of reference data in a supervised learning process to generate at least one artificial radiological image for a plurality of measured radiological images which show an examination region at different time points after an administration of a contrast agent, wherein the at least one artificial radiological image shows blood vessels in the examination region with contrast enhancement and with an unchanging contrast over time compared to the surrounding tissue,
    receiving at least one artificial radiological image from the prediction model, wherein the at least one artificial radiological image shows blood vessels in the examination region with contrast enhancement and with an unchanging contrast over time compared to the surrounding tissue,
    outputting the at least one artificial radiological image.
5. The method according to any of embodiments 1 to 4 above, comprising the steps of
    receiving a plurality of measured radiological images, wherein the radiological images show an examination region at different time points after an administration of a contrast agent, wherein blood vessels in the examination region are depicted with contrast enhancement compared to the surrounding tissue, wherein the contrast enhancement decreases over time,
    generating at least one artificial radiological image, wherein the at least one artificial radiological image shows the same examination region, wherein blood vessels in the examination region are depicted with contrast enhancement compared to the surrounding tissue, wherein the contrast enhancement does not decrease over time,
    outputting the at least one artificial radiological image.
6. The method according to any of embodiments 1 to 5 above, comprising the steps of
    receiving a plurality of measured radiological images, wherein the radiological images show an examination region at different time points after an administration of a contrast agent,
    generating an artificial radiological image by adding up the received radiological images,
    outputting the at least one artificial radiological image.
7. The method according to any of embodiments 1 to 6 above, comprising the steps of
    receiving a plurality of measured radiological images, wherein the radiological images show an examination region at different time points before and/or after an administration of a contrast agent,
    generating a blood vessel model from the received radiological images, wherein the blood vessel model is a representation of the examination region, wherein structures which can be attributed to blood vessels in the examination region have been marked in the blood vessel model,
    generating at least one artificial radiological image by superimposition of at least one measured radiological image on the blood vessel model,
    outputting the at least one artificial radiological image.
8. The method according to embodiment 7 above, wherein a native radiological image of the examination region is superimposed on the blood vessel model.
9. The method according to embodiment 7 above, wherein at least one measured radiological image of the examination region is superimposed on the blood vessel model, wherein the at least one measured radiological image shows the examination region after administration of an intracellular contrast agent, preferably a hepatobiliary contrast agent.
10. The method according to any of embodiments 1 to 9 above, wherein different blood vessels in the at least one artificial radiological image are marked differently.
11. A computer system comprising
    a receiving unit
    a control and calculation unit and
    an output unit
    wherein the control and calculation unit is configured to prompt the receiving unit to receive at least one radiological image, wherein the at least one radiological image shows an examination region of an examination object,
    wherein the control and calculation unit is configured to calculate at least one artificial radiological image on the basis of the at least one radiological image, wherein blood vessels in the at least one artificial radiological image are depicted with contrast enhancement compared to surrounding tissue,
    wherein the control and calculation unit is configured to prompt the output unit to output the at least one artificial radiological image.
12. The computer system according to embodiment 11 above, wherein the control and calculation unit is configured to prompt the receiving unit to receive at least one first measured radiological image of a blood vessel system of an examination object or a portion of the blood vessel system,
    wherein the control and calculation unit is configured to generate a model of the blood vessel system or a portion thereof on the basis of the at least one first measured radiological image, wherein the control and calculation unit is configured to prompt the receiving unit to receive at least one second measured radiological image of an examination region of the examination object, wherein the control and calculation unit is configured to generate at least one third radiological image by superimposition of the model of the blood vessel system or a portion thereof on the at least one second radiological image, wherein the control and calculation unit is configured to prompt the output unit to output the at least one third radiological image.

13. A computer program product comprising a computer program which can be loaded into a memory of a computer, where it prompts the computer to execute the following steps:

receiving at least one radiological image, wherein the at least one radiological image shows an examination region of an examination object, calculating at least one artificial radiological image on the basis of the at least one radiological image, wherein blood vessels in the at least one artificial radiological image are depicted with contrast enhancement compared to surrounding tissue, outputting the at least one artificial radiological image.

14. Use of a contrast agent in a radiological examination method, wherein the radiological examination method comprises the following steps:

administering the contrast agent into a blood vessel of a blood vessel system of an examination object capturing at least one radiological image of the blood vessel system or a portion thereof after administration of the contrast agent generating a model of the blood vessel system or a portion thereof on the basis of the at least one radiological image generating at least one artificial radiological image by superimposition of the model of the blood vessel system or a portion thereof on the at least one radiological image outputting the at least one artificial radiological image.

15. A contrast agent for use in a radiological examination method, wherein the radiological examination method comprises the following steps:

administering the contrast agent into a blood vessel of a blood vessel system of an examination object capturing at least one radiological image of the blood vessel system or a portion thereof after administration of the contrast agent generating a model of the blood vessel system or a portion thereof on the basis of the at least one radiological image generating at least one artificial radiological image by superimposition of the model of the blood vessel system or a portion thereof on the at least one radiological image outputting the at least one artificial radiological image.

16. A kit comprising a contrast agent and a computer program product according to the disclosure according to embodiment 13 above.

The disclosure is elucidated in detail hereinafter with reference to drawings, without any intention to restrict the disclosure to the features or combinations of features shown in the drawings.

FIG. 1 shows, in schematic form and by way of example, one embodiment of the computer system according to the disclosure. The computer system (10) comprises a receiving unit (11), a control and calculation unit (12) and an output unit (13).

A "computer system" is an electronic data processing system that processes data by way of programmable computing rules. Such a system usually comprises a control and calculation unit, often also referred to as "computer", said unit comprising a processor for carrying out logical operations and a memory for loading a computer program, and also peripherals.

In computer technology, "peripherals" refers to all devices that are connected to the computer and are used for control of the computer and/or as input and output devices. Examples thereof are monitor (screen), printer, scanner, mouse, keyboard, joystick, drives, camera, microphone, speakers, etc. Internal ports and expansion cards are also regarded as peripherals in computer technology.

Modern computer systems are frequently divided into desktop PCs, portable PCs, laptops, notebooks, netbooks and tablet PCs, and what are called handhelds (for example smartphones); all of these systems may be used to implement the disclosure.

Inputs into the computer system (e.g. for control by a user) are achieved via input means such as, for example, a keyboard, a mouse, a microphone, a touch-sensitive display and/or the like. Outputs are achieved via the output unit (13), which can be especially a monitor (screen), a printer and/or a data storage medium.

The computer system (10) according to the disclosure is configured to receive measured radiological images and to generate (calculate) artificial radiological images on the basis of the received radiological images.

The control and calculation unit (12) serves for control of the receiving unit (11) and the output unit (13), coordination of the data and signal flows between the various units, processing of radiological images, and generation of artificial radiological images. It is conceivable that multiple control and calculation units are present.

The receiving unit (11) serves for receiving radiological images. The radiological images can, for example, be transmitted from a magnetic resonance imaging system or be transmitted from a computed tomography system or be read from a data storage medium. The magnetic resonance imaging system or the computed tomography system can be a component of the computer system according to the disclosure. However, it is also conceivable that the computer system according to the disclosure is a component of a magnetic resonance imaging system or a computed tomography system. Radiological images can be transmitted via a network connection or a direct connection. Radiological images can be transmitted via radio communication (WLAN, Bluetooth, mobile communications and/or the like) and/or via a cable. It is conceivable that multiple receiving units are present. The data storage medium, too, can be a component of the computer system according to the disclosure or be connected thereto, for example via a network. It is conceivable that multiple data storage media are present.

The radiological images possibly further data (such as, for example, information about the examination object, image-acquisition parameters and/or the like) are received by the receiving unit and transmitted to the control and calculation unit.

The control and calculation unit is configured to generate artificial radiological images on the basis of the received data.

Via the output unit (13), the artificial radiological images can be displayed (e.g. on a monitor), be output (e.g. via a printer) or be stored in a data storage medium. It is conceivable that multiple output units are present.

Figure 2:
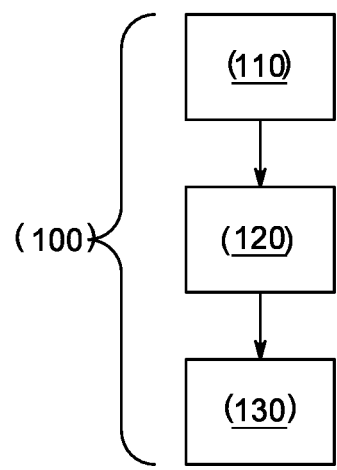

FIG. 2 shows, by way of example and in schematic form, one embodiment of the method (100) according to the disclosure or the steps executed by the computer program product according to the disclosure in the form of a flow chart.

The steps are:
(110) receiving a sequence of measured radiological images, wherein the measured radiological images show an examination region of an examination object at different, consecutive time points after an administration of a contrast agent, wherein the contrast agent leads to a contrast enhancement of blood vessels in the examination region, wherein the contrast enhancement of the blood vessels in the measured radiological images decreases as time increases,
(120) calculating a sequence of artificial radiological images on the basis of the received radiological images, wherein the contrast enhancement of the blood vessels in the artificial radiological images remains unchanged over time,
(130) outputting the artificial radiological images.

Figure 3:
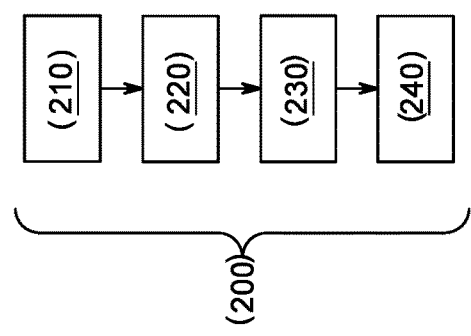

FIG. 3 shows, by way of example and in schematic form, a preferred embodiment of the method (200) according to the disclosure or the steps executed by the computer program product according to the disclosure in the form of a flow chart.

The steps are:
(210) receiving a sequence of measured radiological images, wherein the measured radiological images show an examination region of an examination object at different, consecutive time points after an administration of a contrast agent, wherein the contrast agent leads to a contrast enhancement of blood vessels in the measured radiological images of the examination region, wherein the contrast enhancement of the blood vessels in the measured radiological images falls as time increases,
(220) supplying the radiological images to an artificial neural network, wherein the artificial neural network has been trained on the basis of reference data in a supervised learning process to compensate for a contrast enhancement of blood vessels that falls over time in radiological images,
(230) receiving from the artificial neural network a sequence of calculated radiological images, wherein the calculated radiological images show the examination region at different, consecutive time points, wherein blood vessels in the calculated radiological images are depicted with contrast enhancement, wherein the contrast enhancement of the blood vessels remains constant as time increases,
(240) outputting the calculated radiological images.

Figure 4:
Figure 4:
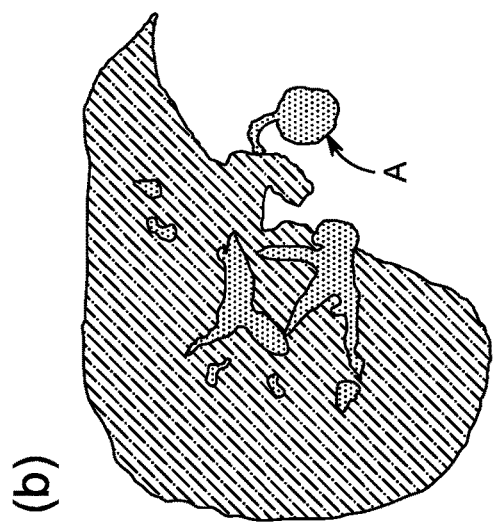
Figure 4:
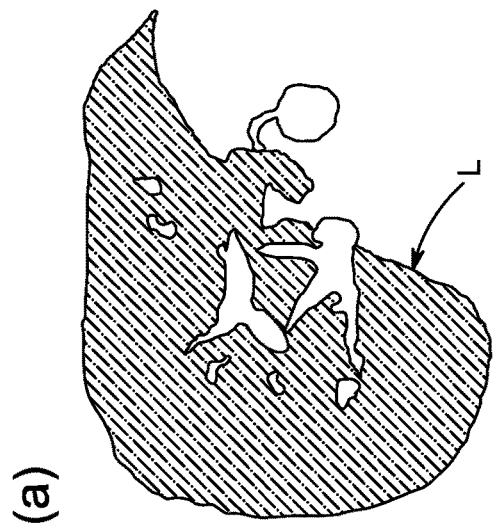

FIGS. 4(a), (b) and (c) show, by way of example and in schematic form, radiological images of a liver after the intravenous administration of a contrast agent into an arm vein of an examination object. In FIGS. 4(a), 4(b) and 4(c), the same cross section through the liver (L) is always depicted at different, consecutive time points. The reference signs entered in FIGS. 4(a), 4(b) and 4(c) apply to all of FIGS. 4(a), 4(b) and 4(c); they are each entered only once merely for the sake of clarity.

In FIGS. 4(a), 4(b) and 4(c), the arteries (A) and veins (V) are depicted with contrast enhancement compared to the surrounding tissue (liver cells). However, the contrast enhancement decreases over time from FIG. 4(a) through FIG. 4(b) to FIG. 4(c).

Figure 5:
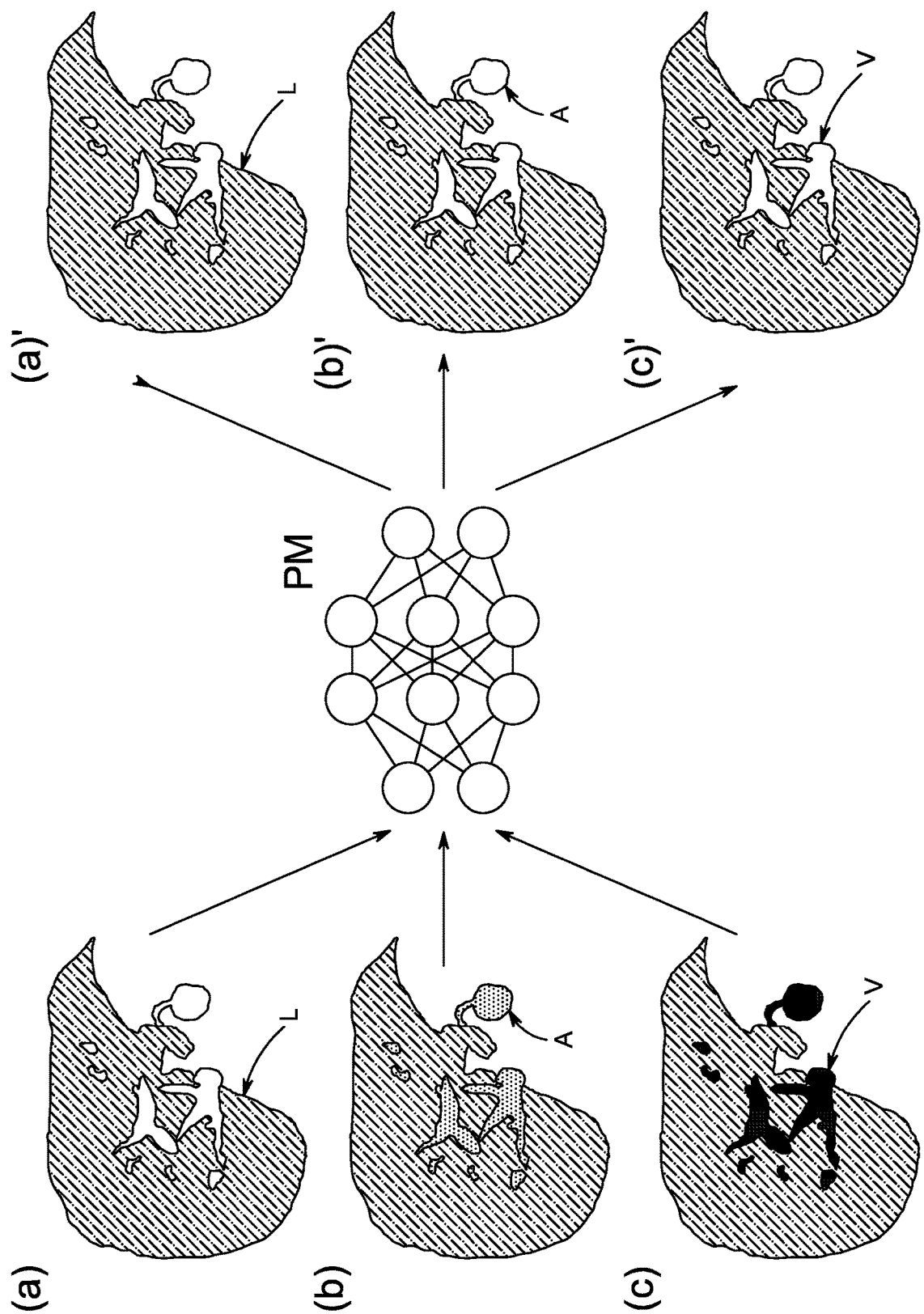

FIG. 5 shows, by way of example in schematic form, the generation of artificial radiological images on the basis of measured radiological images with the aid of a prediction model (PM). The radiological images (a), (b) and (c) of a liver that are depicted in FIG. 5 correspond to the images of the liver that are depicted in FIGS. 4(a), 4(b) and 4(c). Said measured radiological images (a), (b) and (c) are supplied to a prediction model (PM). The prediction model generates three artificial radiological images (a'), (b') and (c') from the three measured radiological images (a), (b) and (c). Whereas the contrast enhancement of the blood vessels (arteries A and veins V) falls over time in the measured radiological images, it remains unchanged over time in the artificially generated radiological images.

Figure 6:
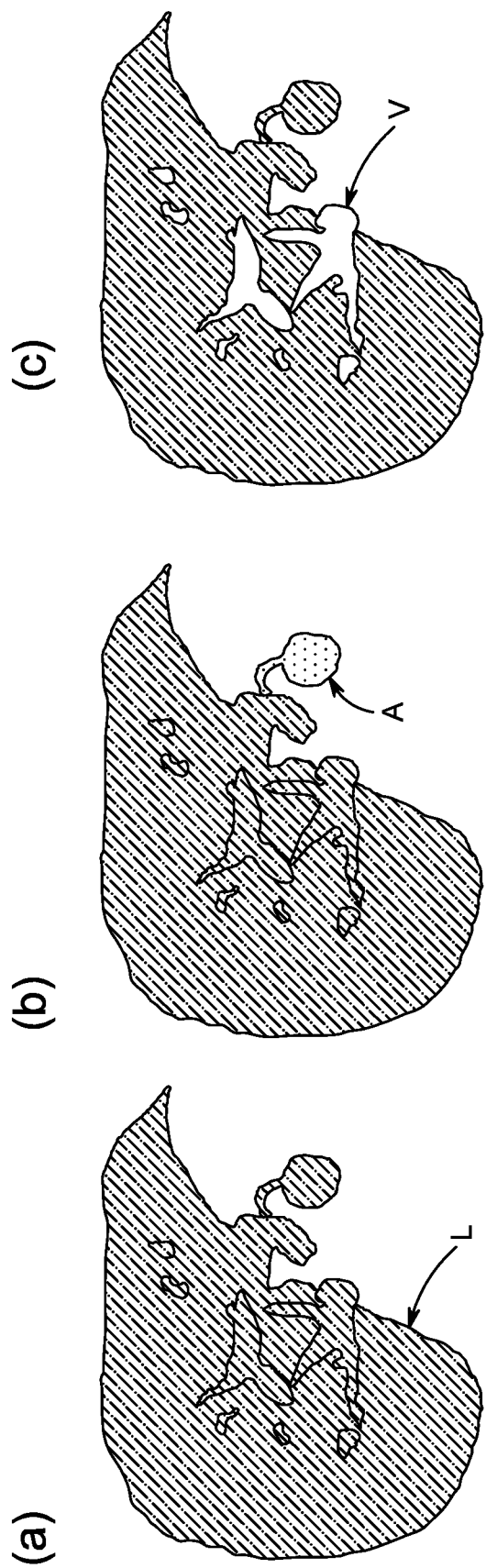

FIGS. 6(a), 6(b) and 6(c) show, by way of example and in schematic form, radiological images of a liver before (6(a)) and after (6(b), 6(c)) the intravenous administration of a contrast agent into an arm vein of an examination object. In FIGS. 6(a), 6(b) and 6(c), the same cross section through the liver (L) is always depicted at different, consecutive time points. The reference signs entered in FIGS. 6(a), 6(b) and 6(c) apply to all of FIGS. 6(a), 6(b) and 6(c); they are each entered only once merely for the sake of clarity.

FIG. 6(a) shows the cross section through the liver (L) before the intravenous administration of a contrast agent. At a time point between the time points depicted by FIGS. 6(a) and 6(b), a contrast agent was administered intravenously as a bolus. This reaches the liver via the liver artery (A) in FIG. 6(b). Accordingly, the liver artery is depicted with signal enhancement (arterial phase). At the time point depicted in FIG. 6(c), the contrast agent reaches the liver via the veins (venous phase).

FIG. 6(a) is thus a native radiological image, FIG. 6(b) is a first radiological image after administration of a contrast agent and FIG. 6(c) is a second radiological image after administration of the contrast agent. In FIG. 6(b), the arteries can be seen particularly well, whereas in FIG. 6(c), the veins can be seen particularly well.

Figure 7:
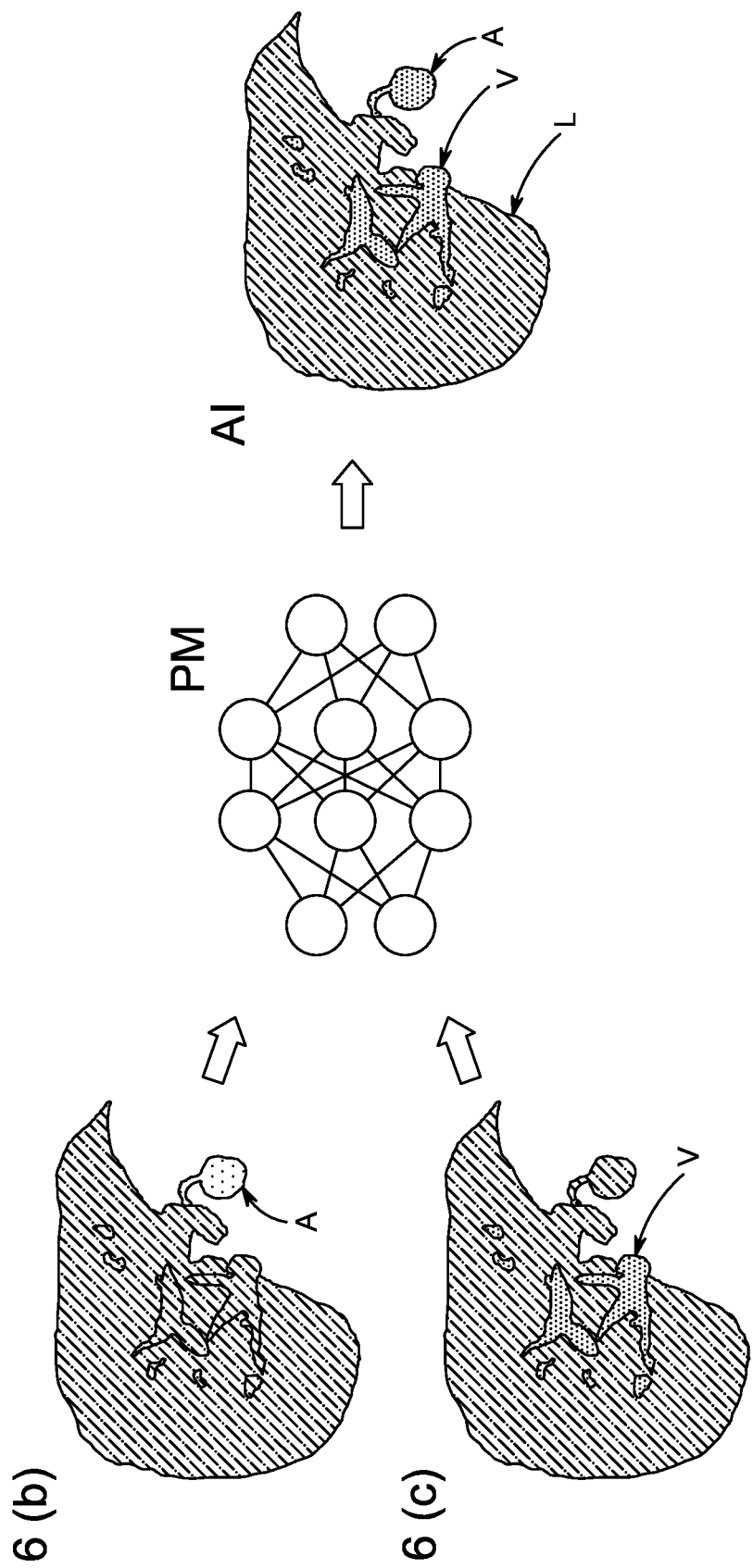

FIG. 7 shows, by way of example and in schematic form, the generation of an artificial radiological image (AI) on the basis of measured radiological images with the aid of a prediction model (PM). The prediction model (PM) has been trained to generate, for at least one measured radiological image which shows an examination region of an examination object, at least one artificial radiological image which shows the examination region after the administration of an intravascular contrast agent. In the present example, the radiological images from FIG. 6(b) and FIG. 6(c) are supplied to the prediction model (PM). The prediction model then automatically generates an artificial radiological image (AI). It shows all blood vessels (arteries A, veins V) with contrast enhancement and with unchanging contrast over time compared to the surrounding tissue.

Figure 8:
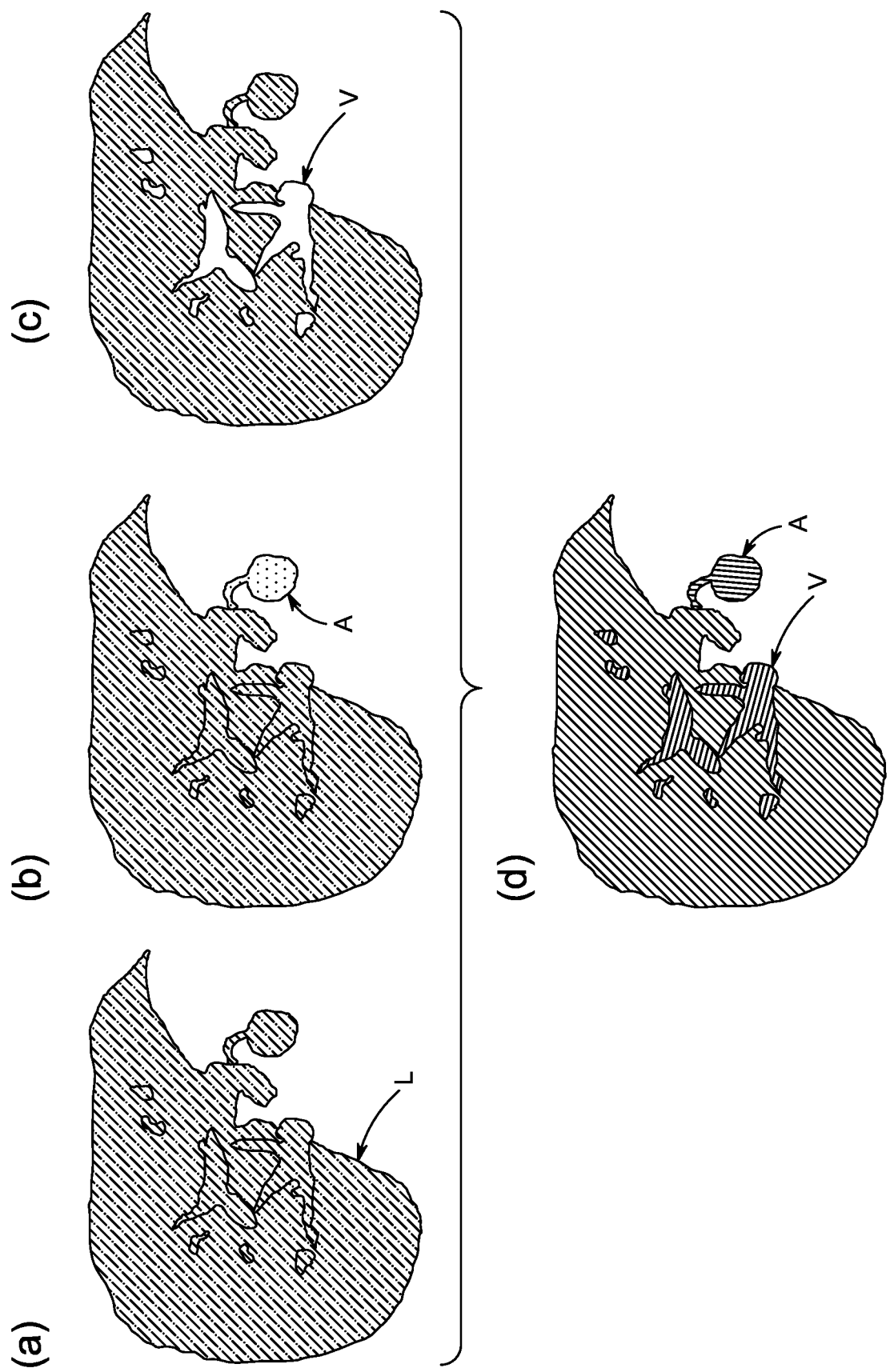

FIG. 8 shows, by way of example and in schematic form, the generation of a blood vessel model from measured radiological images. FIGS. 8(a), 8(b) and 8(c) are identical to FIGS. 6(a), 6(b) and 6(c).

The native radiological image in FIG. 8(a) is combined with the radiological image in FIG. 8(b) and the radiological image in FIG. 8(c) to form a blood vessel model (FIG. 8(d)). This can, for example, be done by generating a difference image of FIG. 8(a) and FIG. 8(b) in a first step (FIG. 8(b)-FIG. 8(a)). In such a difference image, the arteries (A) stand out particularly strongly, whereas all other structures recede into the background. In a further step, a difference image of FIG. 8(*a*) and FIG. 8(*c*) can be generated (FIG. 8(*c*)-FIG. 8(*a*)). In such a difference image, the veins (V) stand out particularly strongly, whereas all other structures recede into the background. In a further step, the two difference images generated can be combined, for example by adding up, to form the blood vessel model (FIG. 8(*d*)). Preferably, the arteries and the veins are marked differently in the blood vessel model (FIG. 8(*d*)) (in the present case, the veins are provided with horizontal hatching, whereas the arteries are provided with vertical hatching).

Figure 9:
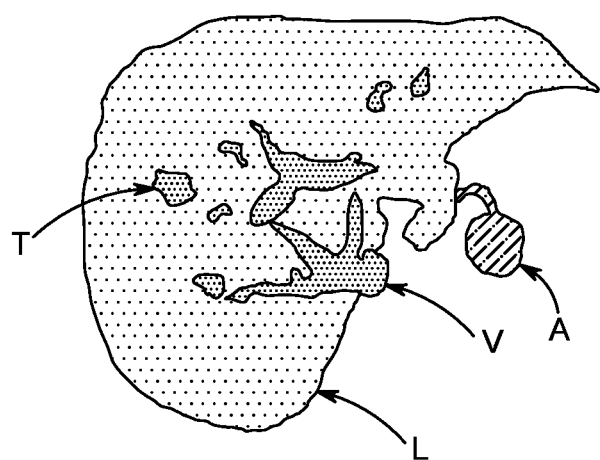

FIG. 9 shows, by way of example and in schematic form, a measured radiological image of a liver (L) after the intravenous administration of a hepatobiliary contrast agent into an arm vein of the examination object. The hepatobiliary contrast medium is taken up by healthy liver cells. The radiological image shown in FIG. 9 shows a cross section of the liver in the hepatobiliary phase, in which the liver cells have already taken up contrast agent. A structure T can be seen, for which it is unclear whether said structure is a blood vessel or a tumor.

Figure 10:
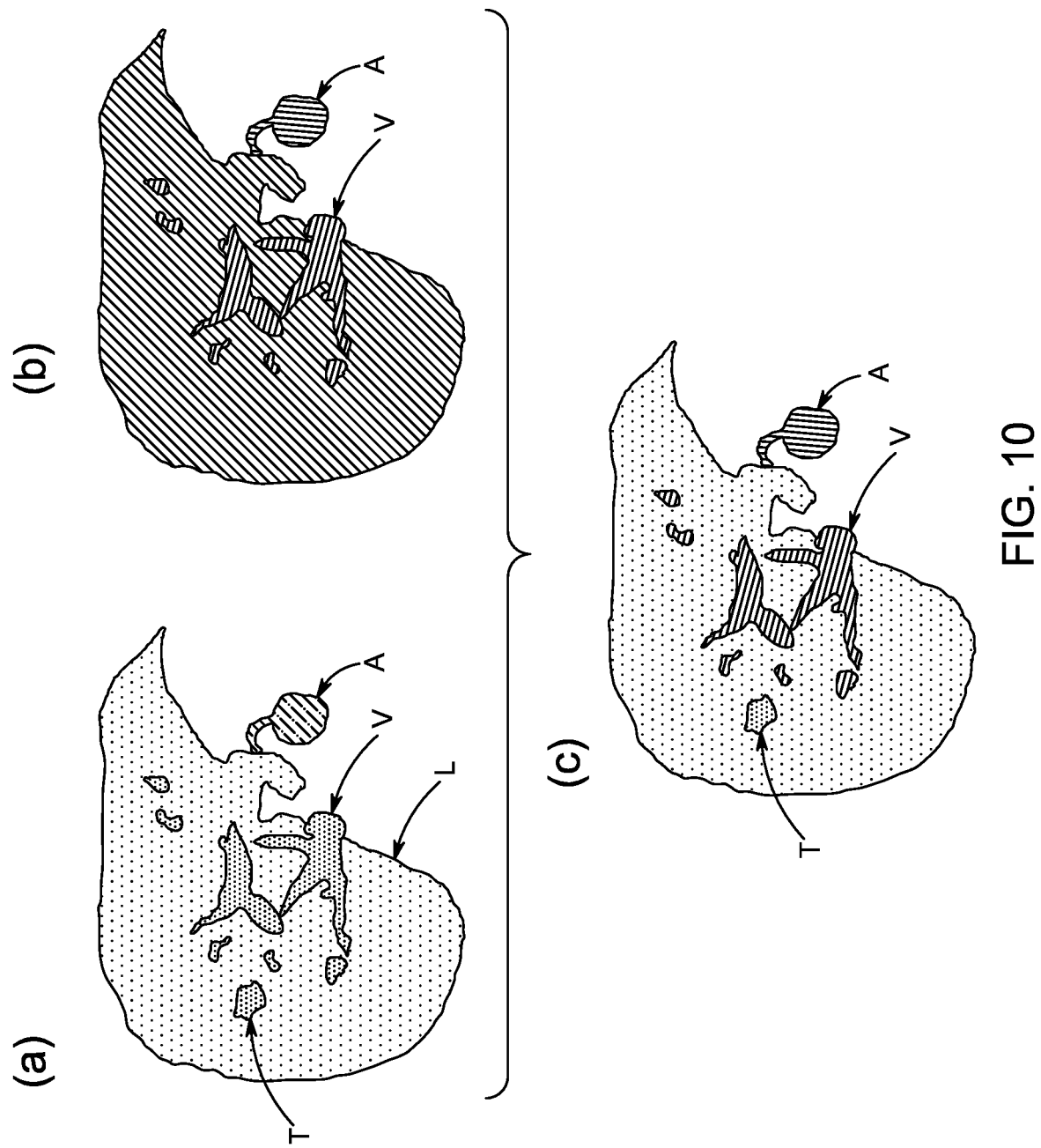

FIG. 10 shows, by way of example and in schematic form, the superimposition of a blood vessel model on a measured radiological image to form an artificial radiological image.

FIG. 10(*a*) shows the measured radiological image of a liver (L) in cross section. FIG. 10(*a*) is identical to FIG. 9. FIG. 10(*b*) shows a blood vessel model. FIG. 10(*b*) is identical to FIG. 8(*d*). FIG. 10(*c*) shows an artificial radiological image. In the case of the artificial radiological image, the pixels of those structures of the blood vessel model which can be attributed to blood vessels replace the corresponding pixels of the measured radiological image. In the artificial radiological image, it can be easily seen which structures can be attributed to healthy liver cells, which structures can be attributed to arteries (A) and which structures can be attributed to veins (V). Furthermore, it can be seen in the artificial radiological image that the structure T is not a blood vessel. It is conceivable that a tumor is present.

The invention claimed is:

1. A computer-implemented method comprising:
   receiving a sequence of measured radiological images, wherein the measured radiological images show an examination region of an examination object at different, consecutive time points after an administration of a contrast agent, wherein the contrast agent leads to a contrast enhancement of blood vessels in the examination region, wherein the contrast enhancement of the blood vessels in the measured radiological images decreases as time increases,
   calculating a sequence of artificial radiological images based on the measured radiological images, wherein the contrast enhancement of the blood vessels in the artificial radiological images remains unchanged over time, and
   outputting the artificial radiological images,
   wherein the calculating the sequence of artificial radiological images comprises:
   supplying the measured radiological images to a prediction model, wherein the prediction model has been trained based on reference data in a supervised learning process to compensate for contrast enhancement of blood vessels that falls over time, wherein the reference data comprise measured radiological images after administration of an extracellular contrast agent and measured radiological images after administration of an intravascular contrast agent and/or artificially generated radiological images in which contrast enhancement of blood vessels that decreases over time in the measured radiological images has been compensated for afterwards by image processing methods, and
   receiving the sequence of artificial radiological images from the prediction model.

2. The method of claim 1, wherein calculating the sequence of artificial radiological images further comprises:
   generating a blood vessel model from the measured radiological images, wherein the blood vessel model is a representation of the examination region, wherein structures which can be attributed to blood vessels in the examination region have been marked in the blood vessel model,
   generating the sequence of artificial radiological images by superimposition of the blood vessel model on the measured radiological images.

3. The method of claim 1, wherein the contrast agent administered is an extracellular contrast agent or an intracellular contrast agent.

4. The method of claim 1, wherein the measured radiological images are magnetic resonance imaging (MRI) images.

5. The method of claim 1, wherein the prediction model is an artificial neural network.

6. A computer system comprising:
   a receiving unit
   a control and calculation unit, and
   an output unit,
   wherein the control and calculation unit is configured to prompt the receiving unit to receive a sequence of measured radiological images, wherein the measured radiological images show an examination region of an examination object at different, consecutive time points after an administration of a contrast agent, wherein the contrast agent leads to a contrast enhancement of blood vessels in the examination region, wherein the contrast enhancement of the blood vessels in the measured radiological images decreases as time increases,
   wherein the control and calculation unit is configured to calculate a sequence of artificial radiological images based on the measured radiological images, wherein the contrast enhancement of the blood vessels in the artificial radiological images remains unchanged over time,
   wherein the control and calculation unit is configured to prompt the output unit to output the artificial radiological images, and
   wherein the calculating the sequence of artificial radiological images comprises:
   supplying the measured radiological images to a prediction model, wherein the prediction model has been trained based on reference data in a supervised learning process to compensate for contrast enhancement of blood vessels that falls over time, wherein the reference data comprise measured radiological images after administration of an extracellular contrast agent and measured radiological images after administration of an intravascular contrast agent and/or artificially generated radiological images in which contrast enhancement of blood vessels that decreases over time in the measured radiological images has been compensated for afterwards by image processing methods, and
   receiving the sequence of artificial radiological images from the prediction model.

7. The computer system of claim 6, wherein the calculation of the sequence of artificial radiological images further comprises:

generating a blood vessel model from the measured radiological images, wherein the blood vessel model is a representation of the examination region, wherein structures which can be attributed to blood vessels in the examination region have been marked in the blood vessel model, and generating the sequence of artificial radiological images by superimposition of the blood vessel model on the measured radiological images.

8. A non-transitory computer-readable storage medium comprising instructions that, when executed by a processor, cause the processor to execute the following:

receive a sequence of measured radiological images, wherein the measured radiological images show an examination region of an examination object at different, consecutive time points after an administration of a contrast agent, wherein the contrast agent leads to a contrast enhancement of blood vessels in the examination region, wherein the contrast enhancement of the blood vessels in the measured radiological images decreases as time increases, calculate a sequence of artificial radiological images based the measured radiological images, wherein the contrast enhancement of the blood vessels in the artificial radiological images remains unchanged over time, and output the artificial radiological images, wherein the calculating the sequence of artificial radiological images comprises:

supplying the measured radiological images to a prediction model, wherein the prediction model has been trained based on reference data in a supervised learning process to compensate for contrast enhancement of blood vessels that falls over time, wherein the reference data comprise measured radiological images after administration of an extracellular contrast agent and measured radiological images after administration of an intravascular contrast agent and/or artificially generated radiological images in which contrast enhancement of blood vessels that decreases over time in the measured radiological images has been compensated for afterwards by image processing methods, and receiving the sequence of artificial radiological images from the prediction model.

9. A kit comprising a contrast agent and the non-transitory computer-readable storage medium according to claim 8.

10. The non-transitory computer-readable storage medium of claim 8, wherein the calculation of the sequence of artificial radiological images further comprises:

generating a blood vessel model from the measured radiological images, wherein the blood vessel model is a representation of the examination region, wherein structures which can be attributed to blood vessels in the examination region have been marked in the blood vessel model, and generating the sequence of artificial radiological images by superimposition of the blood vessel model on the measured radiological images.

11. Use of a contrast agent in a radiological examination method, wherein the radiological examination method comprises:

administering the contrast agent into a blood vessel of a blood vessel system of an examination object, capturing a sequence of radiological images of an examination region of the examination object, wherein the radiological images show the examination region at different, consecutive time points after the administration of the contrast agent, wherein the contrast agent leads to a contrast enhancement of blood vessels in the examination region, wherein the contrast enhancement of the blood vessels in the radiological images falls as time increases, calculating a sequence of artificial radiological images based on the captured radiological images, wherein the contrast enhancement of the blood vessels in the artificial radiological images remains unchanged over time, and outputting the artificial radiological images, wherein the calculating the sequence of artificial radiological images comprises:

supplying the measured radiological images to a prediction model, wherein the prediction model has been trained based of reference data in a supervised learning process to compensate for contrast enhancement of blood vessels that falls over time, wherein the reference data comprise measured radiological images after administration of an extracellular contrast agent and measured radiological images after administration of an intravascular contrast agent and/or artificially generated radiological images in which contrast enhancement of blood vessels that decreases over time in the measured radiological images has been compensated for afterwards by image processing methods, and receiving the sequence of artificial radiological images from the prediction model.

12. The use of claim 11, wherein the calculating the sequence of artificial radiological images further comprises:

generating a blood vessel model from the measured radiological images, wherein the blood vessel model is a representation of the examination region, wherein structures which can be attributed to blood vessels in the examination region have been marked in the blood vessel model, and generating the sequence of artificial radiological images by superimposition of the blood vessel model on the measured radiological images.

* * * * *